United States Patent
Haasl et al.

(10) Patent No.: US 8,691,418 B2
(45) Date of Patent: Apr. 8, 2014

(54) INSULATIVE MEMBER ON BATTERY CATHODE

(75) Inventors: Benjamin J. Haasl, Forest Lake, MN (US); James P. Rohl, Prescott, WI (US); Michael J. O'Phelan, Lutsen, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1757 days.

(21) Appl. No.: 11/140,854

(22) Filed: May 31, 2005

(65) Prior Publication Data

US 2005/0221171 A1    Oct. 6, 2005

(51) Int. Cl.
*H01M 2/18* (2006.01)
*H01M 2/10* (2006.01)
*H01M 2/14* (2006.01)

(52) U.S. Cl.
USPC .......................... 429/130; 429/247; 429/131

(58) Field of Classification Search
USPC .......................... 429/131, 139, 129, 130, 138
See application file for complete search history.

(56) References Cited

U.S. PATENT DOCUMENTS

| | | | |
|---|---|---|---|
| 3,100,164 A * | 8/1963 | Solomon et al. | 429/116 |
| 3,182,238 A | 5/1965 | Toder et al. | |
| 3,201,280 A * | 8/1965 | Yumoto | 429/82 |
| 3,742,938 A | 7/1973 | Stern | |
| 3,803,457 A | 4/1974 | Yamamoto | |
| 3,826,143 A | 7/1974 | Thomas et al. | |
| 3,828,227 A | 8/1974 | Millard et al. | |
| 3,859,574 A | 1/1975 | Brazier | |
| 3,914,666 A | 10/1975 | Schmickl et al. | |
| 3,938,228 A | 2/1976 | Kemkers et al. | |
| 4,047,790 A | 9/1977 | Carino | |
| 4,113,921 A | 9/1978 | Goldstein et al. | |
| 4,131,935 A | 12/1978 | Clement | |
| 4,200,687 A * | 4/1980 | Frode et al. | 429/130 |
| 4,232,099 A | 11/1980 | Sullivan | |
| 4,263,378 A | 4/1981 | Feiman et al. | |
| 4,393,125 A | 7/1983 | Skarstad et al. | |
| 4,394,713 A | 7/1983 | Yoshida | |
| 4,614,194 A | 9/1986 | Jones et al. | |
| 4,616,655 A | 10/1986 | Weinberg et al. | |
| 4,659,636 A | 4/1987 | Suzuki et al. | |
| 4,663,253 A | 5/1987 | Simonton et al. | |
| 4,683,516 A | 7/1987 | Miller | |
| 4,745,039 A | 5/1988 | Yoshinaka | |

(Continued)

FOREIGN PATENT DOCUMENTS

JP         58192271 A   * 11/1983
WO     WO-2004062022 A1    7/2004

OTHER PUBLICATIONS

Definition of "porous"—retrieved from Dictionary.com on Mar. 23, 2011.*
Examiner Annotated Figure 2 of Watanabe.*

(Continued)

*Primary Examiner* — Ula C Ruddock
*Assistant Examiner* — Matthew Van Oudenaren
(74) *Attorney, Agent, or Firm* — Schwegman, Lundberg, & Woessner, P.A.

(57) ABSTRACT

This document discusses, among other things, an insulative member that is configured around a cathode, and methods and assemblies incorporation the insulative member. In an example, the insulative members protect the edge of the cathode material from damage, prevents the migration of cathode material into contact with an anode, or prevents a metal substrate in the cathode from shorting against an adjacent anode.

21 Claims, 13 Drawing Sheets

(56) References Cited

U.S. PATENT DOCUMENTS

| | | |
|---|---|---|
| 4,796,638 A | 1/1989 | Sasaki |
| 4,849,144 A | 7/1989 | McLoughlin |
| 4,931,899 A | 6/1990 | Pruett |
| 4,937,154 A | 6/1990 | Moses et al. |
| 5,116,698 A | 5/1992 | Sears |
| 5,131,388 A | 7/1992 | Pless et al. |
| 5,142,439 A | 8/1992 | Huggett et al. |
| 5,173,375 A | 12/1992 | Cretzmeyer et al. |
| 5,195,019 A | 3/1993 | Hertz |
| 5,279,029 A | 1/1994 | Burns |
| 5,360,684 A | 11/1994 | Duval et al. |
| 5,367,437 A | 11/1994 | Anderson |
| 5,369,547 A | 11/1994 | Evans |
| 5,414,588 A | 5/1995 | Barbee, Jr. et al. |
| 5,415,959 A | 5/1995 | Pyszczek et al. |
| 5,422,200 A | 6/1995 | Hope et al. |
| 5,439,760 A | 8/1995 | Howard et al. |
| 5,458,993 A | 10/1995 | Terao et al. |
| 5,471,087 A | 11/1995 | Buerger, Jr. |
| 5,486,215 A | 1/1996 | Kelm et al. |
| 5,493,259 A | 2/1996 | Blalock et al. |
| 5,503,948 A | 4/1996 | MacKay et al. |
| 5,507,966 A | 4/1996 | Liu |
| 5,522,851 A | 6/1996 | Fayram |
| 5,549,717 A | 8/1996 | Takeuchi et al. |
| 5,628,801 A | 5/1997 | MacFarlane et al. |
| 5,631,102 A | 5/1997 | Spillman et al. |
| 5,645,586 A | 7/1997 | Meltzer |
| 5,660,737 A | 8/1997 | Elias et al. |
| 5,716,729 A | 2/1998 | Sunderland et al. |
| 5,737,181 A | 4/1998 | Evans |
| 5,741,608 A | 4/1998 | Kojima et al. |
| 5,754,394 A | 5/1998 | Evans et al. |
| 5,790,368 A | 8/1998 | Naito et al. |
| 5,855,995 A | 1/1999 | Haq et al. |
| 5,882,362 A | 3/1999 | Muffoletto et al. |
| 5,908,151 A | 6/1999 | Elias |
| 5,930,109 A | 7/1999 | Fishler |
| 5,973,906 A | 10/1999 | Stevenson et al. |
| 6,004,692 A | 12/1999 | Muffoletto et al. |
| 6,032,075 A | 2/2000 | Pignato et al. |
| 6,042,624 A | 3/2000 | Breyen et al. |
| 6,099,600 A | 8/2000 | Yan et al. |
| 6,104,961 A | 8/2000 | Conger et al. |
| 6,110,233 A | 8/2000 | O'Phelan et al. |
| 6,118,651 A | 9/2000 | Mehrotra et al. |
| 6,139,986 A | 10/2000 | Kurokawa et al. |
| 6,157,531 A | 12/2000 | Breyen et al. |
| 6,190,426 B1 | 2/2001 | Thibault et al. |
| 6,191,931 B1 | 2/2001 | Paspa et al. |
| 6,225,778 B1 | 5/2001 | Hayama et al. |
| 6,233,135 B1 | 5/2001 | Farahmandi et al. |
| 6,238,813 B1 | 5/2001 | Maile et al. |
| 6,249,423 B1 | 6/2001 | O'Phelan et al. |
| 6,275,371 B1 | 8/2001 | Yoshio et al. |
| 6,297,943 B1 | 10/2001 | Carson |
| 6,324,049 B1 | 11/2001 | Inagawa et al. |
| 6,330,925 B1 | 12/2001 | Ovshinsky et al. |
| 6,388,866 B1 | 5/2002 | Rorvick et al. |
| 6,413,283 B1 | 7/2002 | Day et al. |
| 6,445,948 B1 | 9/2002 | Somdahl et al. |
| 6,451,073 B1 | 9/2002 | Farahmandi et al. |
| 6,493,212 B1 | 12/2002 | Clarke et al. |
| 6,498,951 B1 | 12/2002 | Larson et al. |
| 6,509,588 B1 | 1/2003 | O'Phelan et al. |
| 6,522,525 B1 | 2/2003 | O'Phelan et al. |
| 6,571,126 B1 | 5/2003 | O'Phelan et al. |
| 6,628,505 B1 | 9/2003 | Andelman |
| 6,632,720 B2 | 10/2003 | Barr et al. |
| 6,674,634 B2 | 1/2004 | O'Phelan et al. |
| 6,684,102 B1 | 1/2004 | O'Phelan et al. |
| 6,687,118 B1 | 2/2004 | O'Phelan et al. |
| 6,699,265 B1 | 3/2004 | O'Phelan et al. |
| 6,709,946 B2 | 3/2004 | O'Phelan et al. |
| 6,763,265 B2 | 7/2004 | O'Phelan et al. |
| 6,833,987 B1 | 12/2004 | O'Phelan |
| 6,869,654 B2 | 3/2005 | Ginkel et al. |
| 7,951,479 B2 | 5/2011 | Kelley et al. |
| 2001/0023145 A1* | 9/2001 | Mito .......................... 439/357 |
| 2003/0165744 A1 | 9/2003 | Schubert et al. |
| 2004/0029302 A1 | 2/2004 | Barr et al. |
| 2004/0048146 A1 | 3/2004 | Adamson |
| 2004/0114311 A1 | 6/2004 | O'Phelan et al. |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2004/0253512 A1* | 12/2004 | Watanabe et al. ............ 429/210 |
| 2005/0010253 A1 | 1/2005 | O'Phelan et al. |
| 2005/0017888 A1 | 1/2005 | Sherwood et al. |
| 2005/0052825 A1 | 3/2005 | O'Phelan |
| 2006/0023400 A1 | 2/2006 | Sherwood |
| 2006/0035152 A1 | 2/2006 | Nishimura et al. |
| 2006/0257726 A1 | 11/2006 | Kelley et al. |
| 2010/0297507 A1 | 11/2010 | Kelley et al. |

OTHER PUBLICATIONS

Examiner Annotated Figure 4 of Solomon.*

Kelley, Shawn, et al., "Method and Apparatus for Porous Insulative Film for Insulating Energy Source Layers", U.S. Appl. No. 11/127,025, filed May 11, 2005, 21 Pages.

O'Phelan, Michael J., et al., "Capacitor Having a Feedthrough Assembly with a Coupling Member", U.S. Appl. No. 09/706,579, filed Nov. 3, 2000, 29 pgs.

Schmidt, Brian L., et al., "Configurations and Methods for Making Capacitor Connections", U.S. Appl. No. 09/706,576, filed Nov. 3, 2000, 26 pgs.

Youker, Nick A., "Method and Apparatus for an Implantable Pulse Generator with a Stacked Battery and Capacitor", U.S. Appl. No. 11/117,952, filed Apr. 29, 2005, 21 Pages.

"U.S. Appl. No. 11/127,025, Non-Final Office Action mailed Jun. 11, 2009", 9 pgs.

"U.S. Appl. No. 11/127,025, Response filed Nov. 2, 2009 to Non-Final Office Action mailed Jun. 11, 2009", 12 pgs.

"U.S. Appl. No. 11/127,025, Notice of Allowance mailed May 7, 2010", 12 pgs.

"U.S. Appl. No. 11/127,025, Examiner Interview Summary mailed Oct. 9, 2009", 3 pgs.

"U.S. Appl. No. 11/127,025, Notice of Allowance mailed Jan. 24, 2011", 9 pgs.

"U.S. Appl. No. 11/127,025, Response filed Mar. 25, 2009 to Restriction Requirement Feb. 25, 2009", 7 pgs.

"U.S. Appl. No. 11/127,025, Restriction Requirement mailed Feb. 25, 2009", 10 pgs.

Moynihan, J. D., "Theory, Design and Application of Electrolytic Capacitors", Theory, Design and Application of Electrolytic Capacitors, Copyright by John D. Moynihan, (1982), 139 pgs.

Shams, A. M, et al., "Titanium hydride formation from Arabian Gulf water", Desalination, vol. 107, (1996), 265-276.

"U.S. Appl. No. 12/852,066, Response filed Jul. 2, 2013 to Restriction Requirement mailed Jun. 13, 2013", 6 pgs.

"U.S. Appl. No. 12/852,066, Restriction Requirement mailed Jun. 13, 2013", 6 pgs.

* cited by examiner

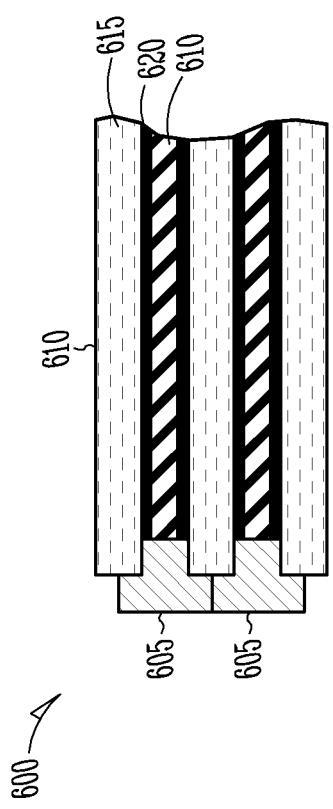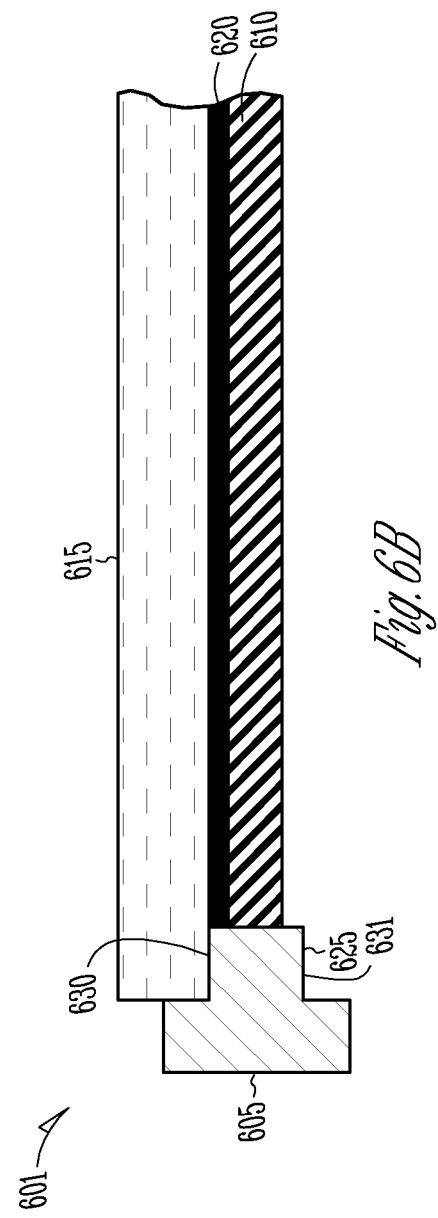

US 8,691,418 B2

INSULATIVE MEMBER ON BATTERY CATHODE

TECHNICAL FIELD

This patent document pertains generally to batteries, and more particularly, but not by way of limitation, to an insulative member on a battery cathode.

BACKGROUND

A patient who is prone to irregular heart rhythms may have a miniature heart device, such as defibrillator and cardioverter, implanted in his or her body. Devices such as these detect the onset of an abnormal heart rhythm and apply a corrective electrical therapy to the heart.

A defibrillator or cardioverter generally includes one or more leads, a battery for supplying power, circuitry for detecting an abnormal heart rhythm, and a capacitor for delivering a burst of electric current through one or more leads to the heart. The battery, circuitry and capacitor are typically contained in a housing. The one or more leads typically have a proximal end coupled to the housing and a distal end secured in or around the heart.

The basic components that make up a battery are an anode, a cathode, and a separator between the anode and the cathode. A battery typically also includes an electrolyte and packaging hardware, which may include a medical device housing.

SUMMARY

An example battery includes an anode, a cathode having a peripheral edge, a separator configured between the anode and the cathode, and at least one insert-molded insulative member molded over at least a first portion of the peripheral edge of the cathode.

Another example battery is a flat-stacked battery including at least one cathode having a peripheral edge, at least one anode located below the at least one cathode, at least one separator located between the at least one anode and the at least one cathode, and at least one insulative member extending over at least a portion of the peripheral edge of the cathode. The at least one insulative member has a lip extending beneath the at least one cathode. The at least one anode is aligned against the lip.

An example implantable device includes a housing, at least one lead, circuitry configured to send and receive electrical impulses through the lead, and a battery configured to provide electrical power to the circuitry. The battery includes at least one cathode having a peripheral edge, at least one anode located below the at least one cathode, at least one separator located between the at least one anode and the at least one cathode, and at least one insulative member extending over at least a portion of the peripheral edge of the cathode. The at least one insulative member has a lip extending beneath the at least one cathode. The at least one anode is aligned against the lip.

An example method includes placing a cathode in a mold, the cathode having a peripheral edge, injecting a polymer into the mold, the polymer surrounding at least a portion of the peripheral edge of the cathode, and removing the cathode and polymer from the mold. The polymer forms at least one insulative member that extends over at least a portion of the peripheral edge of the cathode.

BRIEF DESCRIPTION OF THE DRAWINGS

FIG. 6A is a cross-sectional schematic representation of a stack assembly that includes an exemplary insulative member.

FIG. 6B is a cross-sectional schematic representation of a stack assembly that includes an exemplary insulative member.

DETAILED DESCRIPTION

Figure 8A:
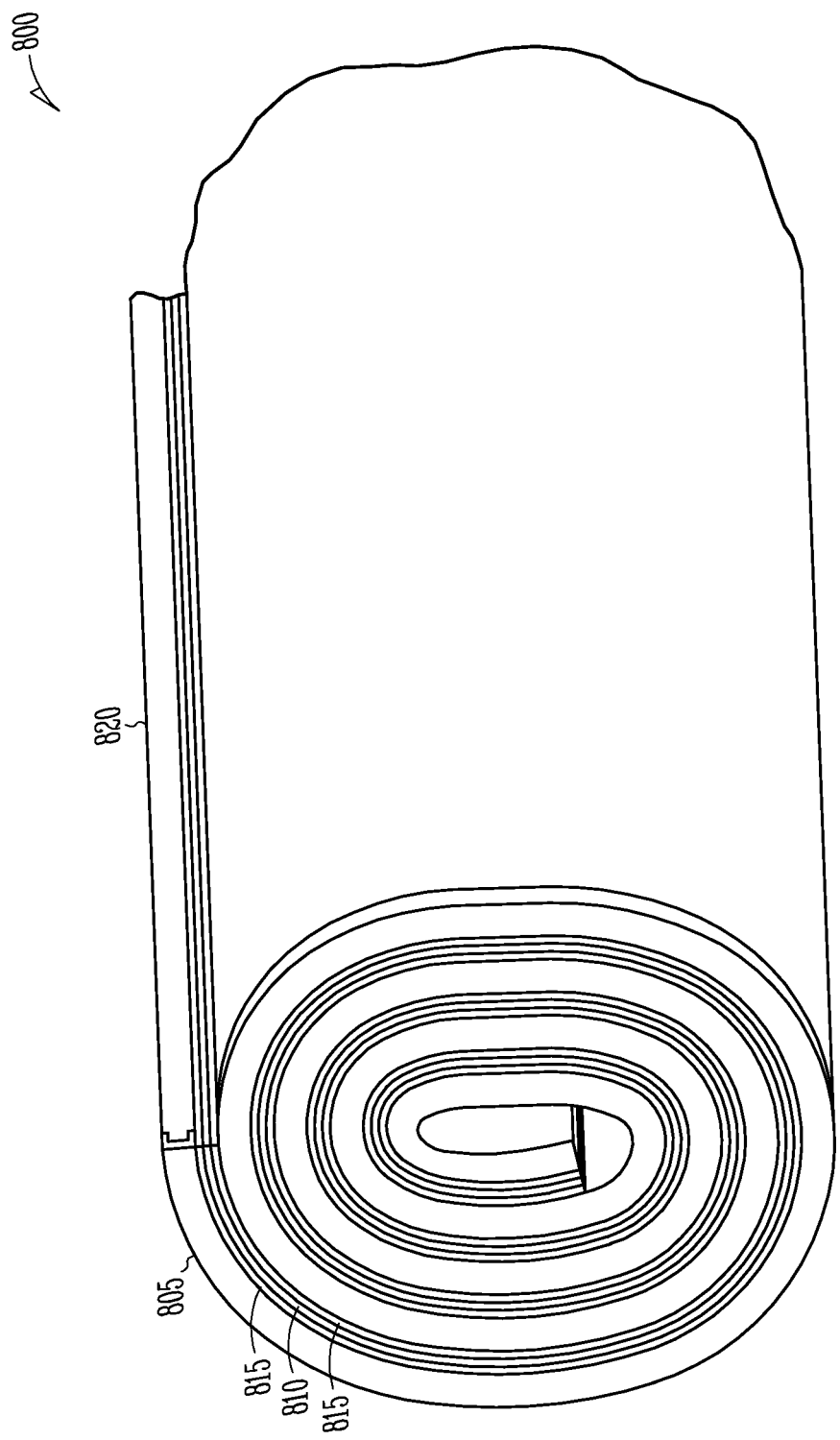
FIG. 8A is a perspective view of a rolled battery including an insulative member.
Figure 8B:
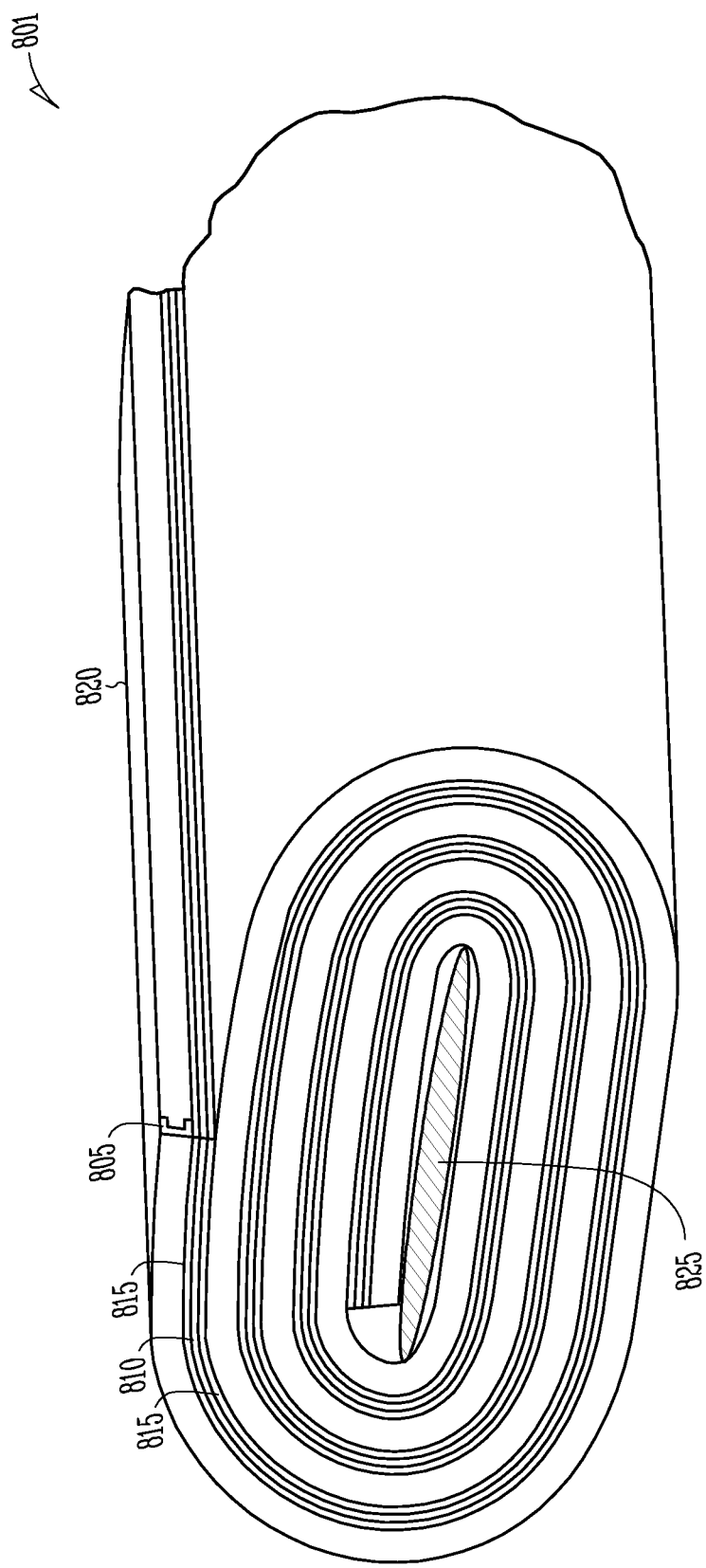
FIG. 8B is a perspective view of an elliptically wound battery including an insulative member.
Figure 9A:
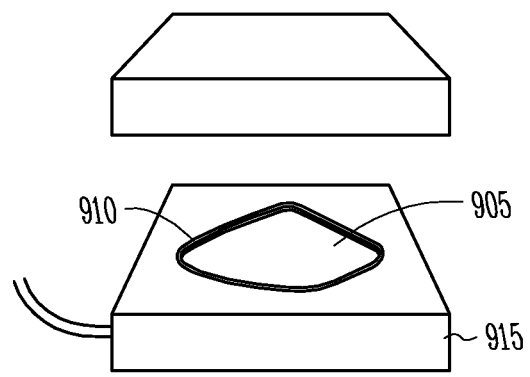
FIGS. 9A, 9B, and 9C illustrate a method of forming an insulative member on a cathode using an insert molding process.
Figure 9B:
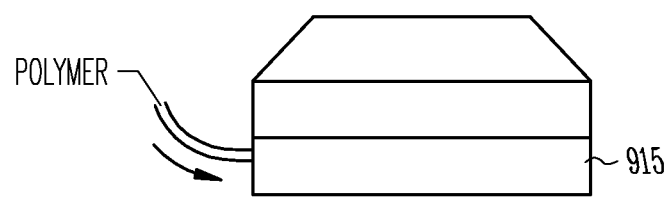
Figure 9C:
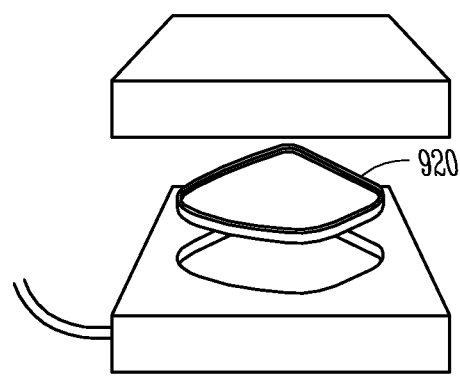

A battery assembly includes at least one insulative member that extends around a portion of a peripheral edge of a cathode. In an example, the cathode and insulative member are part of a medical device, such as the device shown in FIG. 1. Damage, degradation, and shorts can all reduce the life of a battery. In an example, the insulative member protects the edge of the cathode material from damage, prevents the migration of cathode material into contact with an anode, or prevents a metal substrate in the cathode from shorting against an adjacent anode. Exemplary insulative members on cathodes are shown in FIG. 2, FIGS. 3A-3C, and FIG. 4. In an example, the cathode and insulative member are part of a flat stacked battery, as shown, for example, in FIG. 5, FIGS. 6A-6C, and FIGS. 7A-7B. In another example, the cathode and insulative member are incorporated into a rolled battery or elliptically wound battery, as shown in FIGS. 8A and 8B respectively. In an example, one or more insulative members are mechanically pressed onto a cathode. In an example, one or more insulative members are insert molded around a cathode, as illustrated in FIG. 9A-9C.

Figure 1:
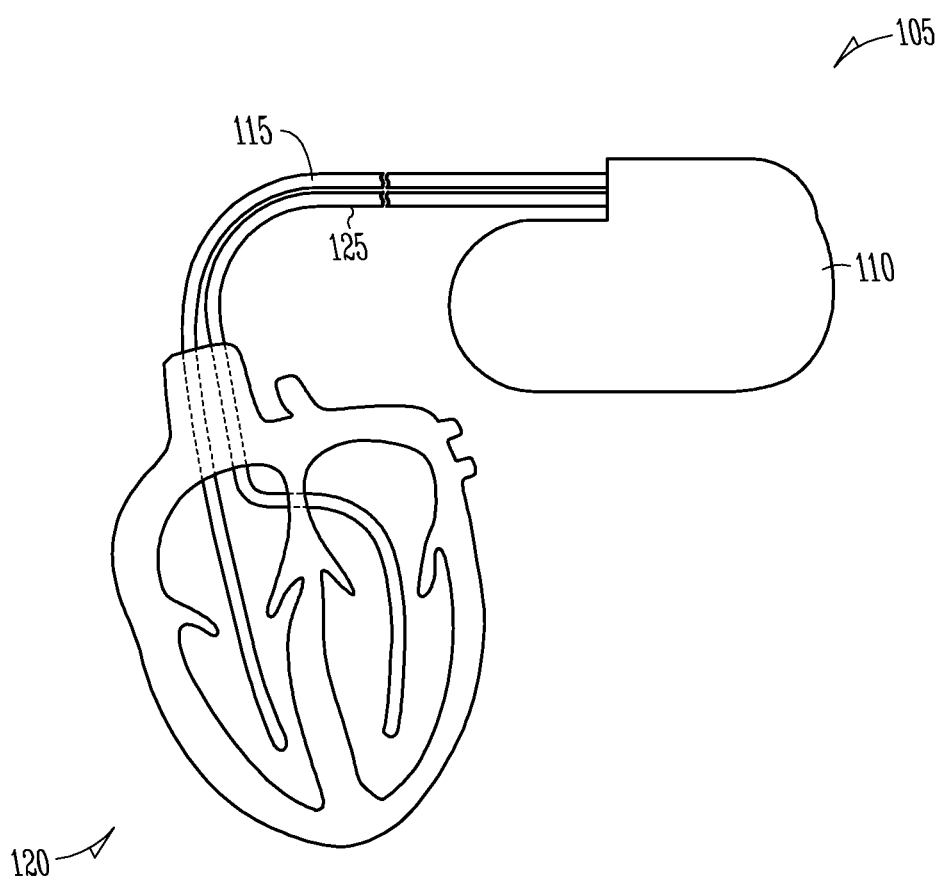
FIG. 1 illustrates a medical device and a heart.

Referring now to FIG. 1, a battery is contained in an exemplary implantable device 105. In an example, the device 105 includes a lead assembly 115 extending into a heart 120 and a housing 110 containing a battery. In an example, the device also includes a second lead 125 that extends into the left side of the heart. In an example, the implantable device includes a defibrillator circuit, and the battery is configured to supply a high energy signal through the defibrillator circuit. A battery typically includes at least one cathode, at least one anode, and at least one separator configured between the cathode and anode. Suitable materials for the separator material include, but are not limited to, a polyethylene, such as Tonen™, or a trilayer (polypropylene, polyethylene, polypropylene) separator material such as Celgard™ 2325, for example. Other chemically inert materials are suitable as well, such as porous polymeric materials. In one embodiment, each separator layer 200 is cut slightly larger than the anode layers (or cathode layers) to accommodate misalignment during the stacking of layers, to prevent subsequent shorting between electrodes of opposite polarity, and to act as an outermost edge for alignment.

Suitable materials for the separator material include, but are not limited to, a polyethylene, such as Tonen™, or a trilayer (polypropylene, polyethylene, polypropylene) separator material such as Celgard™ 2325, for example. Other chemically inert materials are suitable as well, such as porous polymeric materials.

Figure 2:
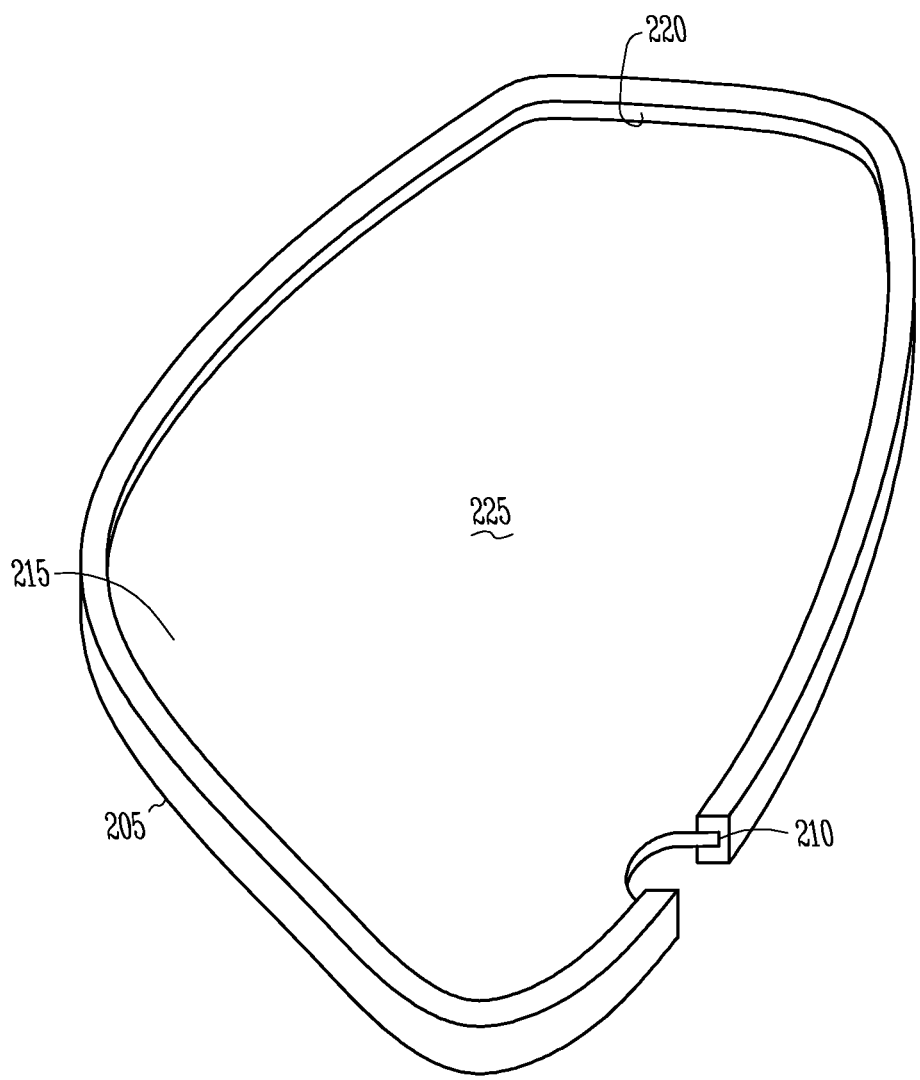
FIG. 2 is a partially cut-away perspective view of a cathode and an insulative member extending around the cathode.

Referring now to FIG. 2, an insulative member 205 extends around at least a portion of a peripheral edge 210 of a cathode 215. In an example, the cathode 215 is made using a pressed powder technique. In another example, the cathode 215 is made using a slurry coating technique. In an example, the insulative member includes a polymer such as polypropylene, polyethylene, or polyimide. The insulative member is insulative in the sense that it is not electrically conductive. In an example, the insulative member protects the peripheral edge 210 of the cathode.

In an example, the insulative member includes an inwardly-facing surface 220. During assembly of a battery, the inwardly-facing surface 220 facilitates alignment of an anode with respect to the cathode. While the inwardly-facing surface 220 is shown perpendicular to a top surface 225 of the cathode, in other examples, the inwardly-facing surface is inclined towards or away from the top surface 225.

Figure 3A:
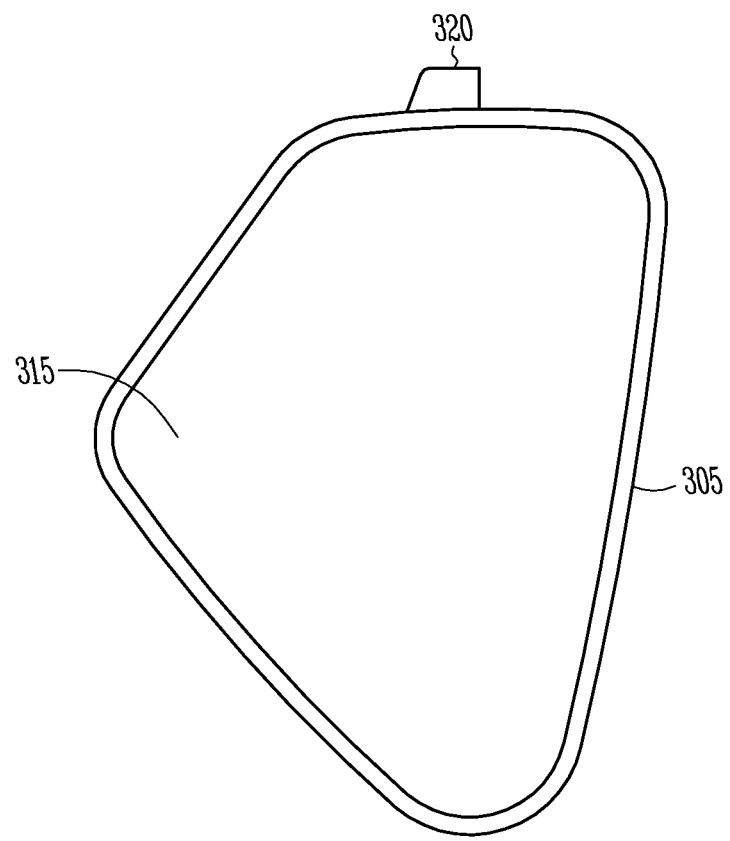
FIG. 3A is a top view of a cathode and an insulative member extending around the cathode.
Figure 3B:
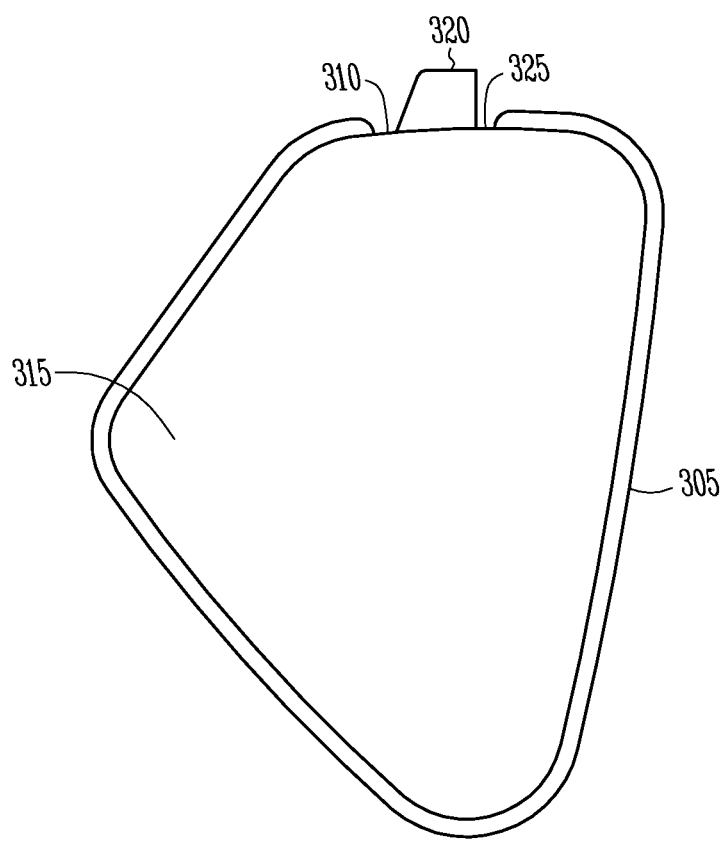
FIG. 3B is a top view of a cathode and an insulative member that does not extend over the entire peripheral edge of a cathode.
Figure 3C:
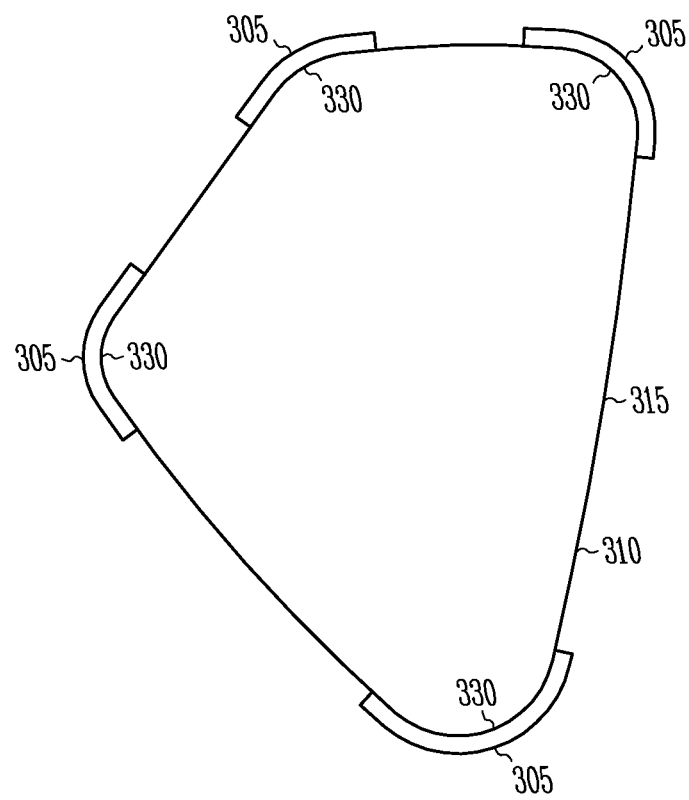
FIG. 3C is a top view of a cathode and a plurality of insulative members located at corner portions of the cathode.

Referring now to FIGS. 3A, 3B, and 3C, top views of three examples of insulative member configurations are shown. FIG. 3A shows a top an insulative member 305 that extends around the entire periphery of a cathode 315. The insulative member extends past an electrical contact 320 that protrudes from an edge of the cathode. In an example, the electrical contact 320 protrudes through the insulative member 305. In another example, the insulative member extends below or above the electrical contact. In an example, the insulative member does not extend around the entire peripheral edge of the cathode. For example, the insulative member shown in FIG. 3B does not extend over a portion 325 of the peripheral edge 310 of the cathode proximate the contact 320. In another example, shown in FIG. 3C, insulative members 305 extend around the peripheral edge 310 proximate corner portions 330 of the cathode, which tend to be more vulnerable to damage and degradation.

Figure 4:
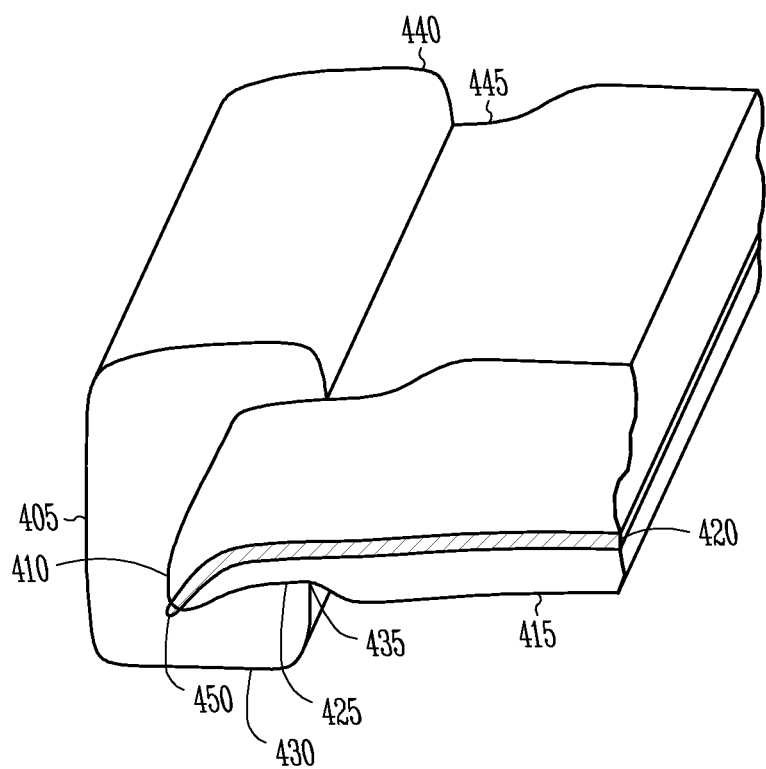
FIG. 4 is a cross-sectional perspective view of a cathode, metal substrate, and an insulative member.

FIG. 4 shows a partial cross-sectional perspective view of an exemplary insulative member 405 that extends over an edge 410 of a cathode 415. The cathode is configured on a metallic substrate 420. A lower lip 430 extends under a lower surface 435 of the cathode. An upper lip 440 extends over an upper surface 445 of the cathode. In an example, the metallic substrate 420 includes expanded metal or a metal mesh. In an example, a portion 450 of the metallic substrate 420 protrudes from the cathode. In an example, the portion 450 that protrudes from the cathode is the end of a wire that is part of a wire mesh substrate. In an example, the portion of the metallic substrate 420 extends into the insulative member 405 or is otherwise confined by the insulative member. Confinement of portions of the metallic substrate that protrude from the cathode prevent shorting between the metallic substrate and adjacent anodes.

Referring again to FIG. 4, a region 425 proximate the peripheral edge of the cathode has a reduced thickness. The reduced thickness permits use of a smaller insulative member, thereby conserving space in the housing of the medical device. In an example, the reduced thickness is created using a coining procedure. In an example, the insulative member 425 is insert molded around the cathode 415. In another example, the insulative member 425 is mechanically pressed onto the cathode 415.

In an example, an insulative member, such as the member shown in FIG. 4, facilitates battery assembly procedures. In an example, the insulative member allows handling of the cathode by the insulative member to avoid damaging the cathode. In an example, the cathode is graspable and positionable by touching only the insulative member. In an example, a cathode is assembled into a flat stack battery, such as the stack shown in FIG. 5, by grasping the insulative member and positioning the cathode in a battery stack. In another example, the insulative member is manipulated to wind the cathode, an anode, and one or more separators into a rolled or elliptically wound battery assembly, as shown in FIGS. 8A and 8B respectively. In an example, the insulative member acts as a bumper that protects the edge of the cathode from impact or abrasion.

Figure 5:
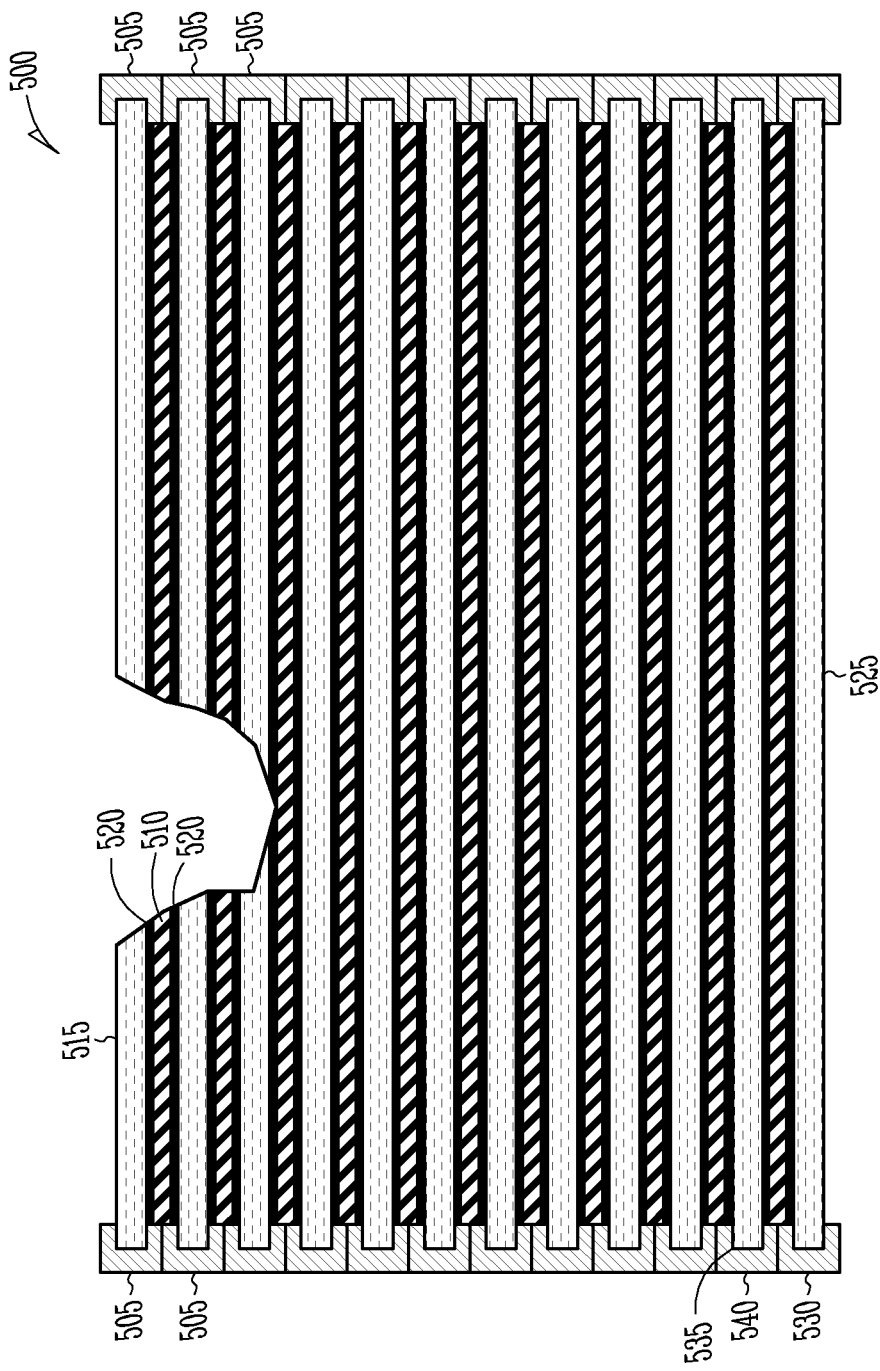
FIG. 5 is a partially cut-away cross-sectional schematic representation of a flat stacked battery including an exemplary insulative member.

Referring now to FIG. 5, a partially cut-away, cross-sectional schematic representation of a flat stacked battery assembly 500 is shown. The battery assembly 500 includes a plurality of insulative members 505 as well as a plurality of anodes 510, cathodes 515, and separators 520. The stack is shown partially cut-away to permit labeling of anodes 510 and separators 520. A separator 520 is provided between each anode 510 and cathode 515 to prevent direct contact between anodes and cathodes. The stacked assembly 500 can be formed, for example, by positioning the bottom cathode 525 by handling an insulative member 530 that is coupled to the bottom cathode, placing a separator on the cathode 525, placing an anode on the separator, and placing a second separator on the anode. The process is then repeated, beginning with a second cathode 535 that is coupled to a second insulative member 540. While eleven cathode layers and ten anode layers are shown in FIG. 5, more or fewer layers can be used. In another example, the layers are wider or thinner than shown in the schematic representation of FIG. 5. In an example, a cathode is 0.018 inches thick, an anode is 0.008 inches thick, and separator is 0.001 inches thick. In an example, a stack includes 12 cathodes, eleven anodes, and eleven separators, and the stack is approximately 0.315 inches thick.

Figure 6C:
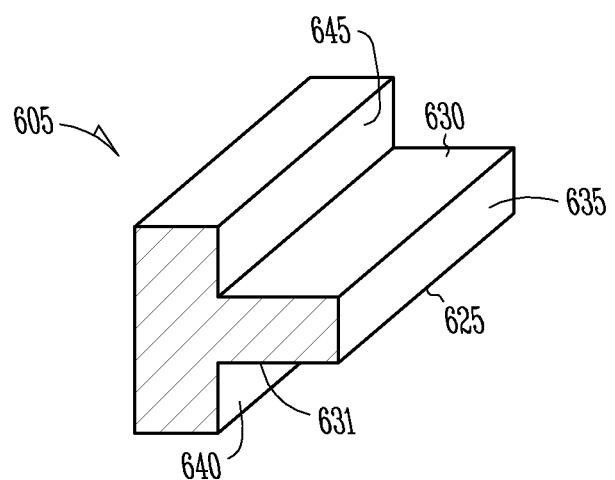
FIG. 6C is a cross-sectional perspective view of an exemplary insulative member.

FIGS. 6A and 6B show partial cross-sectional schematic illustrations of further examples of a stacked battery assembly 600, 601. The stacked battery assembly includes include a plurality of insulative members 605, anodes 610, cathodes 615, and separators 620 configured between the anodes and cathodes. FIG. 6C shows a cross-sectional perspective view of a portion of the insulative member shown in FIGS. 6A and 6B. The insulative member 605 includes a lip 625 that extends beneath a cathode 615. In an example, the separator 620 extends over an upper surface of the lip, and the cathode extends over the separator, as shown in FIG. 6A. In another example, shown in FIG. 6B, the cathode rests directly on the upper surface 630 of the lip 625. In an example, the lip also has a lower surface 631 that contacts a separator or anode below the lip. While two layers are shown for purposes of illustration in FIG. 6A, it is understood that a stack of 12 or more cathodes can be constructed.

Referring now to FIG. 6C, in an example, the lip 625 on the insulative member 605 includes a first inwardly-facing surface 635 that facilitates alignment of an anode with respect to the insulative member. In an example, the insulative member also includes a second inwardly-facing surface 640 that extends below the lip 625 and facilitates alignment of the insulative member with a cathode that is situated below the insulative member. In an example, the insulative member 605 also includes a third inwardly-facing surface 645 that extends above the lip 625 and facilitates alignment of the cathode above the lip 625 with the insulative member 605. In an example, one or more of the surfaces 635, 640, 645 are inclined toward or away from an adjacent anode or cathode.

Figure 7A:
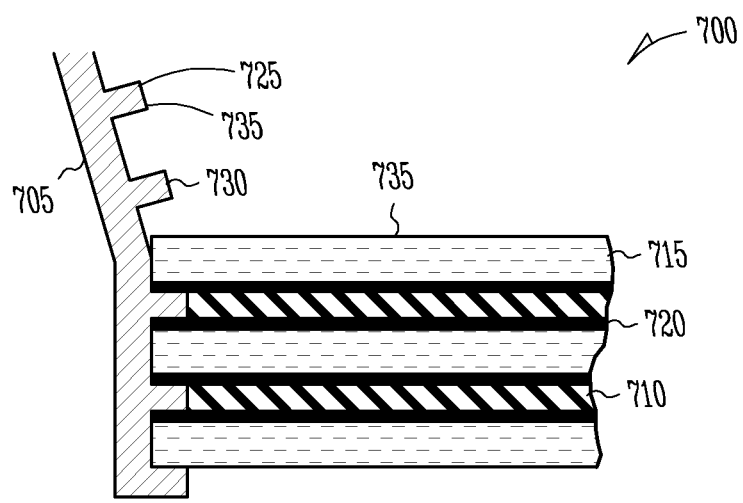
FIGS. 7A and 7B are cross-sectional schematic representations of a stack that includes an exemplary insulative member having a plurality of lips extending under a plurality of respective cathodes.

FIG. 7A shows a partial cross-sectional schematic illustration of another example of a stacked battery assembly 700. The assembly includes at least one insulative member 705 and a plurality of an anodes 710, cathodes 715, and separators 720. The insulative member includes a plurality of lips 725 that extend under the stacked cathodes 715. In an example, the separators 720 extend over at least a portion of the lips 725, as shown in FIG. 7A, and the cathodes 715 rest on the separators. In an alternative example, the cathodes rest directly on the lips.

Figure 7B:
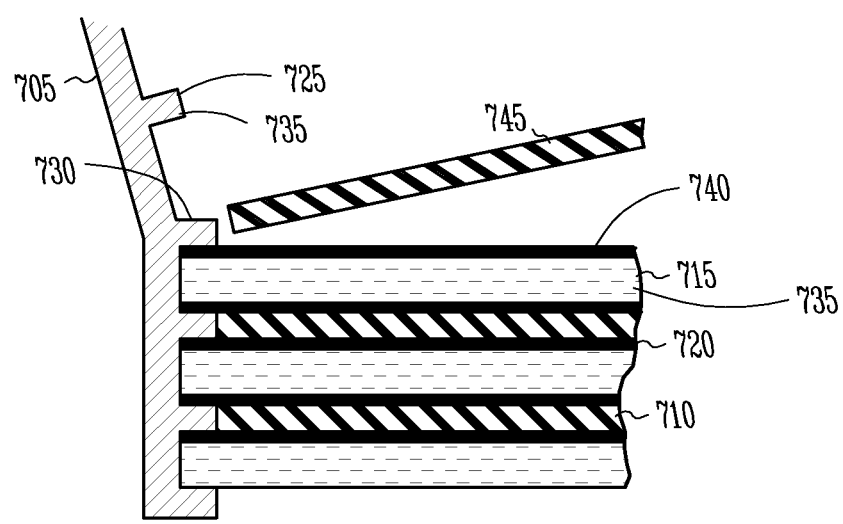

In an example, the insulative member shown in FIG. 7A allows construction of a stack from the bottom up. As shown in FIG. 7A, an upper portion of the insulative member 705 can be bent away from the stack. This allows anodes, cathodes, and separators to be stacked on a lip without obstruction from other lips above. For example, in FIG. 7A, components are stacked on the lower two lips, and a separator and cathode have been stacked on the third lip. To build the next layer in the stack, another separator 740 is assembled on the top cathode 735, and then some of the bending in the insulative member is relieved to bring the fourth lip 730 into position, as shown in FIG. 7B. Next, an anode 745 is aligned against the fourth lip 730 and positioned against the top separator 740. Then, a separator, cathode, and another separator are assembly on top of the anode. This assembly process is repeated until a desired stack height is reached.

In an example, the insulative members shown in FIGS. 5, 6A-C, and 7A-B extend partially or fully around the perimeter of a cathode as shown, for example, in FIGS. 3A and 3B. In another example, multiple insulative members are distributed around the perimeter of the cathode, for example as shown in FIG. 3C.

FIG. 8A shows a rolled battery 800 that includes an insulative members 805, on a proximal end of a cathode 820 that is rolled with a pair of separators 815 and an anode 810. In an example, a second insulative member is provided on a distal end of the cathode. FIG. 8B shows an elliptically would battery 801 that includes an insulative member 805 on a proximal end of a cathode 820 that is wound around a mandrel 825 with a pair of separators 815 and an anode 810. In an example, a second insulative member is provided on a distal end of the elliptically-would cathode In an exemplary method, the insulative members are insert molded or mechanically pressed onto the cathode in a flat configuration, and the cathode is then assembled with the anode and separator and rolled or wound.

FIGS. 9A-9C illustrates a method of insert molding an insulative member around a cathode. A cathode 905 for a stacked, rolled, or elliptically wound battery is inserted into a cavity 910 in a mold 915, as shown in FIG. 9A. The mold 915 is closed, as shown in FIG. 9B, and polymer is inserted into the cavity in the mold. The polymer flows around the cathode 905. The polymer forms one or more insulative members 920 around the cathode. The cathode and insert-molded insulative member(s) are removed from the mold, as shown in FIG. 9C. In an example, this process is repeated for a plurality of cathodes. In an example, cathodes are grasped by the insulative member and arranged in a stack with other battery components, such as anodes and separators.

Examples of the various cathodes, insulative members, and battery assemblies shown and described in this application can be used in an implantable medical device, such as a defibrillator or cardioverter. The cathodes, insulative members, and battery assemblies can also be used in other implantable medical devices that deliver an electrical therapy to parts of the body other than the heart, as well as in non-implantable devices.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A battery comprising:
   an anode;
   a cathode disposed in a stack with the anode, the cathode having a peripheral edge and including material disposed on a substrate;
   a battery separator that is porous and that is sandwiched between the anode and the cathode in the stack, the battery separator having a first face disposed against the anode and a second face, opposite the first face, disposed against the cathode; and
   a first cathode assembly including at least one insulative member disposed over a first edge of the cathode to confine the edge, the at least one insulative member extending around at least a first portion of a periphery of the cathode while extending around a major face of the cathode to define a cavity,
   wherein the cathode and the anode are arranged in the stack in alignment, free to move with respect to one another, with the anode disposed against a lip of the at least one insulative member, in the cavity, with the at least one insulative member facilitating alignment of the anode with respect to the cathode.

2. The battery of claim 1, wherein the at least one insulative member includes a first portion molded around the first portion of the peripheral edge of the cathode, and a second portion molded around a second portion of the peripheral edge of the cathode displaced from the first portion, the cathode graspable by the first and second portions of the at least one insulative member.

3. The battery of claim 2, wherein the first portion of the peripheral edge of the cathode includes a first corner of the cathode, and the second portion of the peripheral edge of the cathode includes a second corner of the cathode.

4. The battery of claim 1, wherein the cathode includes a metal substrate and a cathode material on the metal substrate, a portion of the metal substrate protruding through the cathode material at the peripheral edge of the cathode, the portion of the metal substrate molded into the insulative member.

5. The battery of claim 1, wherein the at least one insulative member aligns the anode with the cathode.

6. The battery of claim 1, wherein the battery is adapted for assembly into an implantable device.

7. The battery of claim 1, comprising a plurality of anodes, a plurality of cathodes, a plurality of battery separators, and a plurality of insulative members configured to form a flat stacked battery.

8. A flat-stacked battery assembly comprising:
   at least one cathode having a peripheral edge and including material disposed on a substrate;
   at least one anode disposed in a stack with the cathode;
   at least one battery separator that is porous sandwiched between the at least one anode and the at least one cathode in the stack and against the at least one anode and the at least one cathode; and a first cathode assembly including at least one insulative member extending around at least a portion of a periphery of the edge of the cathode while extending around a major face of the first cathode, the insulative member having a lip extending toward the anode and beneath the at least one cathode to define a cavity, wherein the at least one cathode and the anode are arranged in the stack in alignment, free to move with respect to one another, with the anode disposed against a lip of the at least one insulative member, in the cavity, with the at least one insulative member facilitating alignment of the anode with respect to the cathode.

9. The flat-stacked battery assembly of claim 8, wherein the lip on the insulative member includes an upper surface proximate a first cathode above the lip, and a lower surface proximate a second cathode below the lip.

10. The flat-stacked battery assembly of claim 9, wherein a first battery separator is positioned between the upper surface of the lip and the first cathode, and a second battery separator is positioned between the lower surfaced of the lip and the second cathode.

11. The flat-stacked battery assembly of claim 8, wherein the cathode includes a metal substrate and a cathode material on the metal substrate, a portion of the metal substrate protruding through the cathode material at the peripheral edge of the cathode, the insulative member covering the portion of the metal substrate.

12. The flat-stacked battery assembly of claim 8, wherein the lip of the insulative member includes an inwardly-facing surface that aligns at least one anode with respect to the insulative member.

13. The flat-stacked battery assembly of claim 8, comprising a plurality of anodes, cathodes, battery separators, and insulative members arranged in a stack, the insulative members aligning the anodes with the cathodes.

14. The flat-stacked battery assembly of claim 8, including a first cathode and a second cathode, the insulative member include a first lip extending beneath the first cathode and a second lip extending beneath the second cathode.

15. An implantable device comprising:
a housing;
at least one lead;
circuitry configured to send and receive electrical impulses through the lead; and
a battery configured to provide electrical power to the circuitry, the battery including:
at least one cathode having a peripheral edge;
at least one anode disposed in a stack with the cathode and including material disposed on a substrate;
at least one battery separator that is porous and that is sandwiched between the at least one anode and the at least one cathode in the stack and against the at least one anode and the at least one cathode; and
a first cathode assembly including at least one insulative member extending around at least a portion of a periphery of the edge of the cathode while extending around a major face of the first cathode, the insulative member having a lip extending toward the anode and beneath the at least one cathode to define a cavity;
wherein the cathode and the anode are arranged in the stack in alignment, free to move with respect to one another, with the anode disposed against a lip of the at least one insulative member, in the cavity, with the at least one insulative member facilitating alignment of the anode with respect to the cathode.

16. The implantable device of claim 15, comprising a plurality of anodes, a plurality of cathodes, a plurality of battery separators, and a plurality of insulative members configured to form the battery.

17. The implantable device of claim 16, wherein the insulative member is insert molded around the cathode.

18. The flat-stacked battery assembly of claim 8, wherein the at least one insulative member includes a first portion molded around the first portion of the peripheral edge of the cathode, and a second portion molded around a second portion of the peripheral edge of the cathode displaced from the first portion, the cathode graspable by the first and second portions of the at least one insulative member.

19. The flat-stacked battery assembly of claim 18, wherein the first portion of the peripheral edge of the cathode includes a first corner of the cathode, and the second portion of the peripheral edge of the cathode includes a second corner of the cathode.

20. The implantable device of claim 15, wherein the at least one insulative member includes a first portion molded around the first portion of the peripheral edge of the cathode, and a second portion molded around a second portion of the peripheral edge of the cathode displaced from the first portion, the cathode graspable by the first and second portions of the at least one insulative member.

21. The implantable device of claim 20, wherein the first portion of the peripheral edge of the cathode includes a first corner of the cathode, and the second portion of the peripheral edge of the cathode includes a second corner of the cathode.

* * * * *